United States Patent
Nita et al.

[11] Patent Number: 5,916,192
[45] Date of Patent: Jun. 29, 1999

[54] ULTRASONIC ANGIOPLASTY-ATHERECTOMY CATHETER AND METHOD OF USE

[75] Inventors: Henry Nita, Mission Viejo; Timothy Mills, Belvedere Tiburon, both of Calif.

[73] Assignee: Advanced Cardiovascular Systems, Inc., Santa Clara, Calif.

[21] Appl. No.: 08/387,996

[22] Filed: Feb. 13, 1995

Related U.S. Application Data

[60] Continuation-in-part of application No. 08/094,416, Jul. 19, 1993, Pat. No. 5,397,301, which is a division of application No. 07/640,190, Jan. 11, 1991, Pat. No. 5,304,115, and application No. 08/255,513, Jun. 8, 1994, Pat. No. 5,474,530, which is a division of application No. 07/911,651, Jul. 10, 1992, Pat. No. 5,324,255.

[51] Int. Cl.⁶ ................................................. A61B 17/20
[52] U.S. Cl. ........................ 604/22; 607/97; 607/122; 606/169; 606/171; 604/48; 604/53
[58] Field of Search .................... 601/2.4; 607/97, 607/122; 128/660.01, 663.01; 604/22, 48, 53; 606/171, 169

[56] References Cited

U.S. PATENT DOCUMENTS 4,223,676  9/1980  Wuchinich et al. ................. 604/22 X
5,342,292  8/1994  Nita et al. ................................. 604/22

*Primary Examiner*—Wynn Wood Coggins
*Assistant Examiner*—N. Kent Gring
*Attorney, Agent, or Firm*—Fulwider Patton Lee & Utecht, LLP

[57] ABSTRACT

An ultrasonic device and method for removing obstructive matter from an anatomical structure or passageway (e.g., blood vessel). The device comprises an elongate pliable catheter having a distal tip member attached to the distal end thereof, and an ultrasound transmission member which extends longitudinally therethrough to carry ultrasound from the proximal end of the catheter to the distal tip member. The distal tip member has a concave indentation formed in the distal surface thereof, and at least one inlet passageway extending therethrough in communication with a catheter lumen to facilitate suctioning of severed matter which becomes located within the concave indentation of the distal tip. The device may further incorporate means for infusing fluid (e.g., irrigation fluid, medicaments) separately or concurrently with the aspiration of the severed obstructive matter.

33 Claims, 3 Drawing Sheets

ULTRASONIC ANGIOPLASTY-ATHERECTOMY CATHETER AND METHOD OF USE

RELATED APPLICATIONS

This application is a continuation-in-part of U.S. application Ser. No. 08/094,416, filed Jul. 19, 1993 now U.S. Pat. No. 5,397,301 which is a division of Ser. No. 640,190 filed Jan. 11, 1991 now U.S. Pat. No. 5,304,115 and of U.S. patent application Ser. No. 08/255,513 filed Jun. 8, 1994, now U.S. Pat. No. 5,474,530 which is a division of Ser. No. 911,651, filed Jul. 10, 1992 and issued on Jun. 28, 1994 as U.S. Pat. No. 5,324,255.

FIELD OF THE INVENTION

The present invention pertains generally to medical equipment and more particularly to an atherectomy catheter having an ultrasound transmission member extending therethrough such that ultrasonic energy may be delivered to the distal end of the catheter to facilitate the atherectomy procedure.

BACKGROUND OF THE INVENTION

The prior art has included a number of ultrasonic catheters which are insertable into the mammalian body and usable to deliver ultrasonic energy for purposes of ablating obstructive material from anatomical cavities or passageways, or for other therapeutic purposes.

Examples of ultrasonic treatment catheters and related apparatus include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al.), 4,920,954 (Alliger, et al.), 5,267,954 (Nita), as well as other patent publications WO87-05739 (Cooper), WO89-06515 (Bernstein, et al.), WO90-0130 (Sonic Needle Corp.), EP316789 (Don Michael, et al.), DE3,821,836 (Schubert) and DE2,438,648 (Pohlman).

Additionally, ultrasound transmitting catheters may be utilized to deliver ultrasonic energy to mammalian blood vessels for the purpose of preventing or reversing vasospasm, as described in U.S. Pat. No. 5,324,255.

The prior art has also included a number of atherectomy devices which are insertable into blood vessels and usable to cut, shave or otherwise sever obstructive matter from the walls of the blood vessel. Such atherectomy devices typically include aspiration channels for suctioning the severed matter from the lumen of the blood vessel. Examples of atherectomy devices which have heretofore been know include those described in U.S. Pat. No. 5,100,423 (Fearnot), Additionally, U.S. Pat. No. 4,808,153 (Parisi) has described a device for removing placque from arteries wherein a hollow tip member is mounted on the distal end of a tubular catheter, and an ultrasound source is connected to the proximal end of the catheter to cause the entire catheter, including the distal tip, to undergo vibratory movement. Such vibratory movement of the hollow distal tip member ostensibly creates heat which serves to emulsify obstructive matter which is located on the walls of an artery adjacent the vibrating hollow tip member. The emulsified matter is subsequently suctioned or withdrawn, in the proximal direction, through the hollow tip member and through the lumen of the catheter.

Although the device described in U.S. Pat. No. 4,808,153 (Perisi) is purportedly useable to remove obstructive matter from the walls of a blood vessel, the device disclosed in such prior United States patent is believed to be of less than optimal design for all intravascular applications. Accordingly, there remains a need for a new ultrasonic angioplasty catheter capable of utilizing ultrasound-induced vibratory motion to sever or separate obstructive matter from the walls of blood vessels or other anatomical passageways, and which includes means for promptly removing the severed or separated matter from the lumen of the blood vessel or anatomical passageway.

SUMMARY OF THE INVENTION

In accordance with the present invention, there is provided an ultrasonic device and method for removing obstructive matter from an anatomical cavity or passageway, such as a blood vessel. The device of the present invention generally comprises an elongate pliable catheter body having a distal tip member attached to the distal end thereof. An ultrasound transmission member, such as a metal wire, extends longitudinally through the catheter body to transmit ultrasonic vibratory movement from the proximal end of the catheter body, to the distal tip member. In this regard, the proximal end of the ultrasound transmission member is connectable to an ultrasonic transducer or other ultrasound generating device. The ultrasound transmission member is substantially unattached to the catheter body, such that the ultrasound transmission member may vibrate or move independent of the catheter body. The distal tip member may be attached to the distal end of the catheter body such that, ultrasonic vibratory movement transmitted to the distal tip member may also cause a distal portion of the catheter body to vibrate or move. A concave indentation is formed on the distal face of the distal tip member, and at least one aspiration passageway extends longitudinally through the distal tip member, from the distal face thereof to the proximal end thereof, in communication with a lumen of the catheter body such that matter which becomes located within the concave indentation of the distal tip member may be aspirated, in the proximal direction, through the aspiration passageway and through the catheter body. The ultrasonic device of the foregoing character insertable into the desired anatomical cavity or passageway (e.g., blood vessel) and advance to a point where the distal tip member is adjacent a quantity of obstructive matter to be removed. Thereafter, ultrasonic energy is passed through the ultrasound transmission member to the distal tip member, thereby causing ultrasonic vibratory movement of the distal tip member. The catheter is then further advanced such that the concave indentation in the distal face of the distal tip member comes in contact with the obstructive matter, and the ultrasonic vibratory movement of the distal tip member causes the obstructive matter to be separated or severed thereby. The separated or severed obstructive matter is then aspirated through the aspiration passageways, and through the catheter, thereby effecting complete removal of such matter.

Further in accordance with the invention, the elongate pliable catheter body of the ultrasonic device of the foregoing character may comprise an outer tube having a hollow lumen of a lumenal diameter, and an inner tube having an outer surface of an outer diameter. The inner tube is disposed within the lumen of the outer tube, and the distal ends of both tubes are affixed or positioned in abutment with the distal tip member. The aspiration passageway(s) of the distal tip member is in communication with the lumen of the inner tube, such that severed particles of obstructive matter may be suctioned through the aspiration passageway and through the lumen of the inner tube. Additional fluid infusion passageways may be formed through the distal tip member, in communication with the lumenal surface of the outer tube. In this regard, irrigation fluid, medicaments or other fluid may be infused through such lumenal space and out of the outlet passageway(s) formed in the distal tip member.

Further in accordance with the invention, there is provided a method of removing obstructive matter from an anatomical passageway, said method comprising the steps of:

a) providing an ultrasonic catheter device which comprises:
   an elongate pliable catheter body having a proximal end, a distal end, and at least one lumen extending longitudinally therethrough;
   a distal tip member attached to the distal end of said catheter body, said distal tip member having a distal surface, a concave indentation being formed in said distal surface;
   an ultrasound transmission member extending longitudinally through said catheter body to transmit ultrasound from an ultrasound source located adjacent the proximal end of said catheter body, through said catheter body, to said distal tip member;
   at least one aspiration passageway extending longitudinally through said distal tip member from the proximal surface thereof to the distal surface thereof, said aspiration passageway being in communication with a lumen of said catheter such that matter which becomes located within the concave indentation of said distal tip member may be aspirated, in the proximal direction, through said passageway and through said lumen of said catheter.

b) inserting said catheter body into said anatomical passageway wherein said obstructive matter is located;

c) advancing said catheter body to a point where said distal tip member is located adjacent the obstructive matter to be removed;

d) passing ultrasound through said ultrasound transmission member through said distal tip member, thereby causing said distal tip member to undergo ultrasonic vibratory movement;

e) advancing said catheter body such that the concaved distal surface of said distal tip member comes into contact with said obstructive matter, and such that the ultrasonic vibratory movement of said distal tip member facilitates severance of a portion of said obstructive matter; and f) causing a severed portion of said obstructive matter to be aspirated in the proximal direction, through said aspiration passageway, and through a lumen of said catheter body.

Additionally the method may include the step of infusing irrigation fluid or medicaments into the region where the obstructive matter is located. Such infusion of irrigation fluid or medicaments may occur separately from, or contemporaneously with, the severing, separation and/or removal of the obstructive matter.

Further objects and advantages of the present invention will become apparent to those skilled in the art upon reading and understanding of the following detailed description and the accompanying drawings.

BRIEF DESCRIPTION OF THE DRAWINGS

FIG. 3, is an enlarged longitudinal sectional view of a distal portion of the catheter shown in FIG. 1.

DETAILED DESCRIPTION OF THE PREFERRED EMBODIMENT

Figure 1:
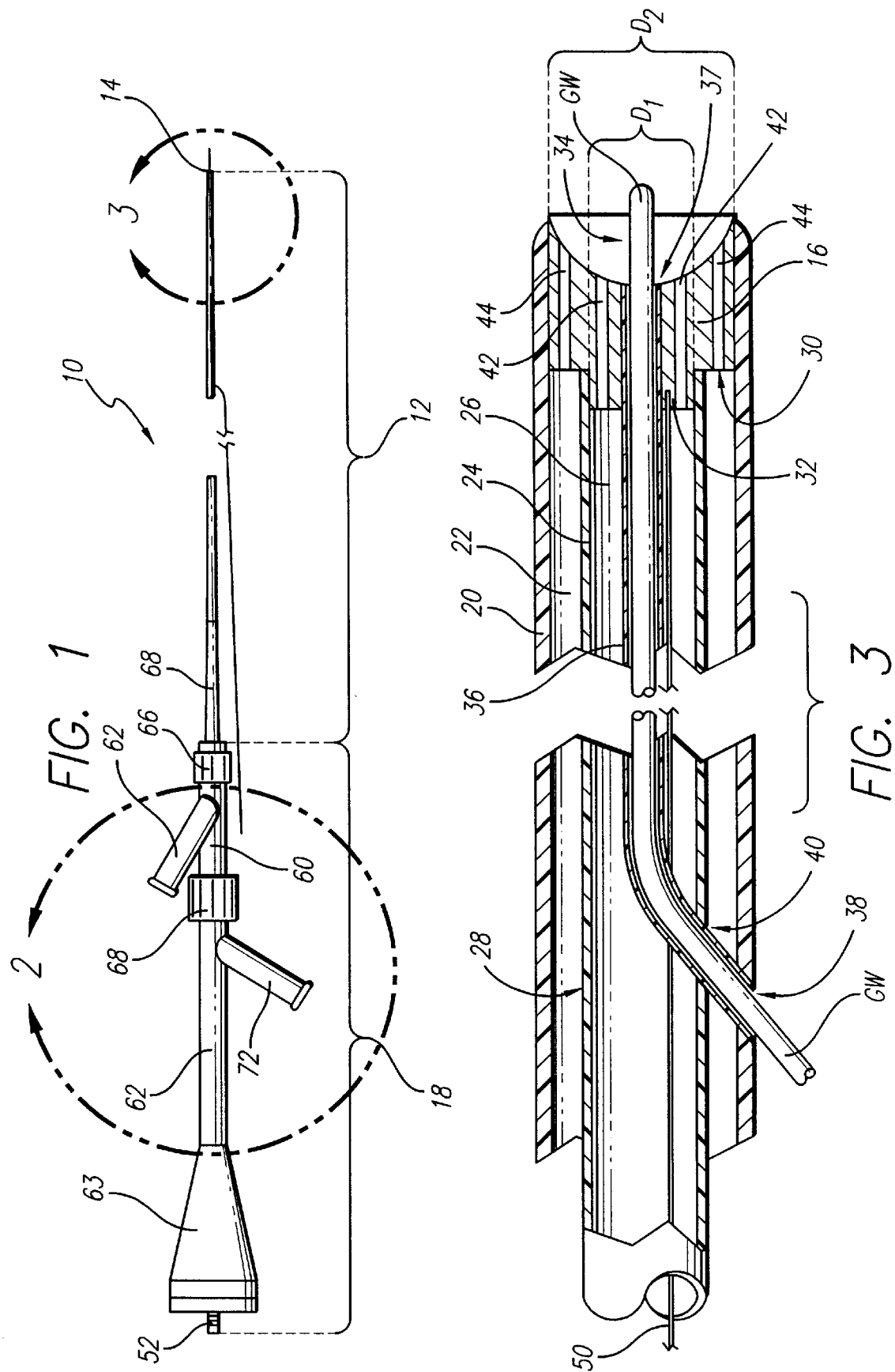
FIG. 1, is an elevation view of a preferred ultrasound angioplasty-atherectomy catheter of the present invention.

The following detailed description of and the accompanying drawings are provided for purposes of describing and illustrating presently preferred embodiments of the invention only, and are not intended to limit the scope of the following claims in any way.

As shown in the drawings, the presently preferred ultrasonic atherectomy catheter 10 of the present invention comprises an elongate pliable catheter body 12 having at least one hollow lumen 14 extending longitudinally therethrough. A distal tip member 16 is mounted within or on the distal end of the catheter body 12. A proximal connector assembly 18 is mounted on or connected to the proximal end of the catheter body 12 to facilitate connection of the catheter device 10 to an ultrasound transducer or other device capable of generating ultrasonic vibratory movement. In the embodiment shown, the catheter body 12 is formed of an outer tube 20 having an outer tube lumen 22 extending longitudinally therethrough, and an inner tube 24 which has an inner tube lumen 26 extending longitudinally therethrough. The inner tube 24 is preferably positioned co-axially within the lumen 22 of the outer tube 20, such that an annular peripheral portion of the outer tube lumen 22 surrounds the outer surface 28 of the inner tube 24.

The outer tube 20 and inner tube 24 are concomitantly connected or held in abutment with the distal tip member 16, such that the respective distal ends of the outer 20 and inner 24 tubes are securely held in their desired coaxial positions. In the embodiment shown, the distal tip member 16 comprises a generally cylindrical rigid body having an annular shoulder 30 formed around the proximal surface thereof, so as to define a generally cylindrical inner region 32 which protrudes in the proximal direction from the center of the distal tip member 16. The diameter $D_1$ of the cylindrical central projection 32 is substantially the same as the inner diameter of the distal end of the inner tube 24, and the distal end of the inner tube 24 is fitted over the central projection 32, with the distal tip of the inner tube abutting against shoulder 30. The outer diameter $D_2$ of the remaining portion of the tip member 16 is substantially the same of the inner diameter of the outer tube 20, such that the remaining body of the distal tip members 16 may be securely fitted within the distal end of the outer tube 20, as shown. Adhesive, heat fusing techniques, or other fusion method may be utilized to securely hold the distal tip member 16 within the distal end of the outer tube 20. Similarly, adhesive, heat fusing or other fusion technique may be utilized to securely hold the distal end of the inner tube 24 in contact with the central projection 32 on the proximal end of the distal tip member 16.

The frontal surface of the distal tip member 16 is provided with a concave indentation 34.

A guidewire passage bore 37 is formed longitudinally through the center of the distal tip member 16, and a guidewire tube 36 extends therethrough. The distal end of the guidewire tube 36 opens through a distal guidewire aperture formed in the center of the concave indentation 34, at the distal end of the catheter 10. The proximal end of the guidewire tube 36 is affixed within or about a proximal guidewire passage aperture 38. In the embodiment shown in the drawings, the proximal guidewire aperture 38 is formed in the sidewall of the outer tube 20, at a location approximately 10–30 cm from the distal end DE of the catheter body 12. A corresponding passage hole or opening 40 is formed in the wall of the inner tube 24, to permit the guidewire tube 36 to exit therethrough. Such passage or opening 40 in the wall of the inner tube 24 is fused or sealed about the outer surface of the guidewire tube 36, thereby preventing fluid leakage through the passage or opening 40, about the guidewire tube 36. It will be appreciated that the specific embodiment shown in the drawings is a "monorail" type of catheter, wherein the guidewire tube 36 extends through only the distal-most portion of the catheter body 12. Alternative "over the wire" embodiments of the invention may also be provided wherein the guidewire tube 36 extends longitudinally through the entire catheter body 12, and wherein the proximal end of the guide wire tube 36 is affixed to or opens through a guidewire entry aperture or sidearm located in the proximal connector assembly 18 of the catheter device 10.

In the "monorail" embodiment shown in the drawings, a guidewire GW, such as a standard cardiovascular guidewire of the type commonly used in modern clinical medicine having an outer diameter of 0.008–0.025 inches, may be inserted into the guidewire bore 37, and the catheter device 10 may then be advanced in the distal direction over the guidewire GW such that the proximal end of the guidewire GW will emerge through the proximal guidewire aperture 38. In this manner, the catheter device 10 may be advanced over a prepositioned guidewire in accordance with standard cardiovascular catheterization technique.

An ultrasound transmission member 50 extends longitudinally through the lumen 26 of the inner tube 24 and is connected or held in abutment, at its distal end, with the distal tip member 16. The proximal end of the ultrasound transmission member 50 is connected to or held in abutment with a sonic connector 52 which is formed on or extends from the proximal connector assembly 18. When an ultrasound transducer, or other device capable of generating ultrasonic vibratory movement is connected to the sonic connector 52, the ultrasonic vibratory movement emitted thereby is transmitted through the ultrasound transmission member 50, to the distal tip member 16.

In the preferred embodiment, the ultrasound transmission member 50 is preferably formed of a metal alloy, or other material, which exhibits superelastic properties within the range of operating temperatures normally encountered by the ultrasound transmission member 50 during use. One suitable superelastic material usable to form the ultrasound transmission member 50 is a nickel-titanium alloy having 50.8 atomic percent nickel, balance titanium.

The preferred proximal connector assembly 18 comprises a distal portion 60, a proximal portion 62, and a sonic connector housing portion 63. The distal portion 60 comprises a tubular hard plastic tube having a fluid/debris aspiration sidearm 62 extending at an angle therefrom. An aperture or opening 64 is formed in the rigid tubular body of the distal portion 60 such that fluid/debris may be aspirated from the lumen 22 of the outer tube 20, through aspiration sidearm 62, via hole or aperture 64. A distal nut 66 and pliable plastic sleeve 68 are attached about the outer surface of the proximal portion of the outer tube 20, thereby securely fastening the outer tube 20 to the distal portion 60 of the proximal connector assembly 18.

Figure 2:
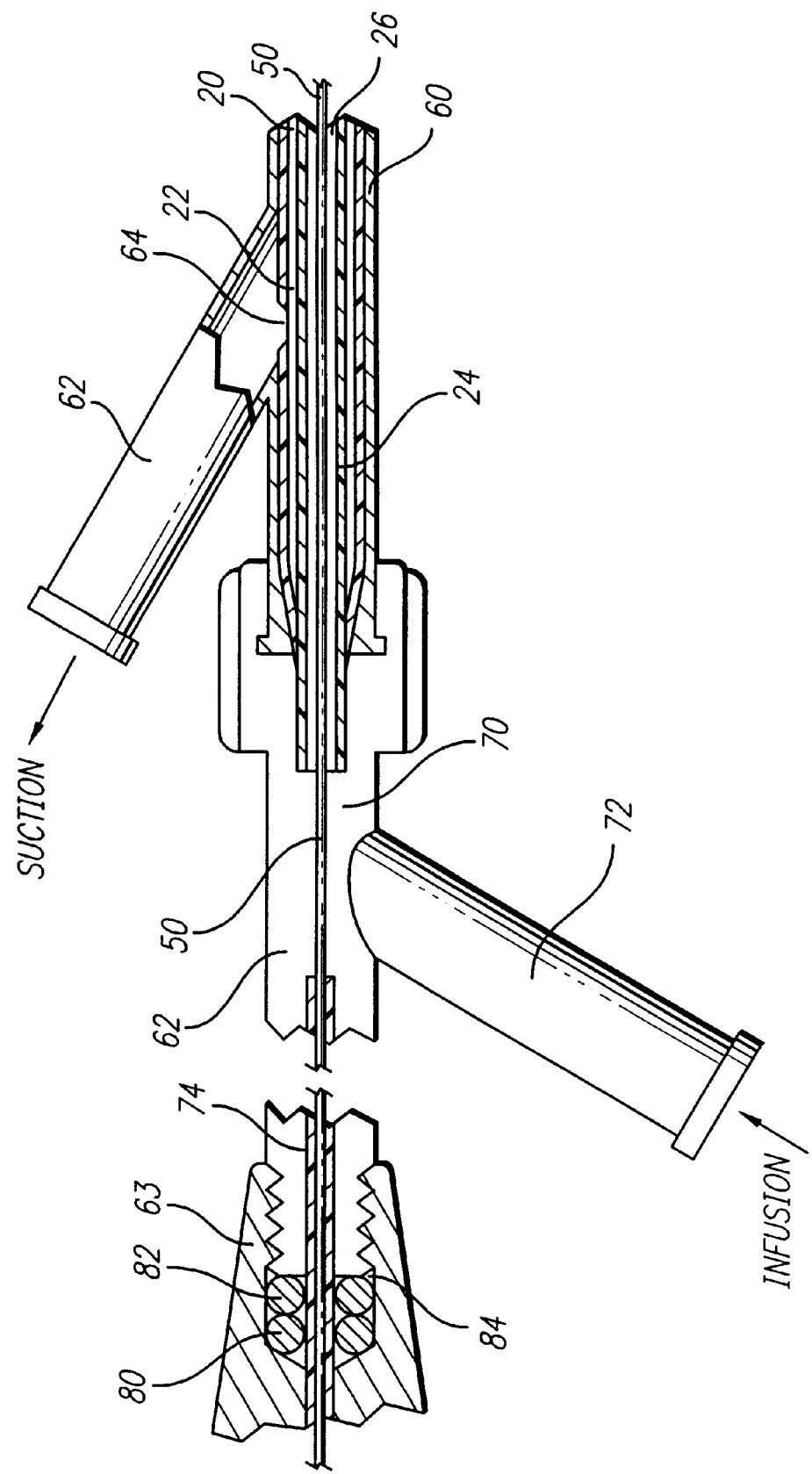
FIG. 2, is an enlarged longitudinal sectional view of a proximal portion of the catheter shown in FIG. 1.

As shown in FIG. 2, the outer tube 20 and inner tube 24 extend longitudinally through the distal portion 60 of the proximal connector assembly 18, to a point adjacent the proximal nut 68 which conjoins the proximal portion 62 to the distal portion 60. At that location, the distal end of the outer tube 20 is fused, or compressively held in contact with, the outer surface of the inner tube 24, so as to prevent fluid within the lumen 22 of the outer tube 20, from leaking in the proximal direction beyond the location of second nut 68. The proximal portion 62 of the proximal connector assembly 18 comprises a rigid tubular plastic body, and the lumen 26 of the inner tube 24 extends and opens into the inner bore 70 of the proximal portion 62, as shown. A fluid infusion sidearm 72 extends from the rigid tubular body of the proximal portion 62, to permit infusion of fluid into the bore 70 of the proximal portion 62, and into and through the lumen 26 of the inner tube 24.

The sonic connector 52 of the proximal connector assembly 18 is housed within a connector housing 63, which connector housing 63 is threadably mounted on the proximal end of the proximal portion 62. A pliable plastic tube 74 extends through the sonic connector housing 63, and protrudes partially into the hollow inner bore 70 of the proximal portion 62, as shown. The ultrasound transmission member 50 extends from the sonic connector 52, through the pliable plastic tube 74, through the hollow inner bore 70 of the proximal portion 62, and into the lumen 26 of the inner tube 24. Such ultrasound transmission member 50 then continues longitudinally though the lumen of the inner tube 24, to its distal end which, as described above, is affixed to or held in abutting contact with the distal tip member 16 of the catheter device 10.

O-rings 80, 82 are positioned within a threaded frontal cavity 84, formed in the distal portion of the sonic connector housing 63. The proximal end of the proximal portion 62 is threaded, and is received within the threaded frontal bore 84 of the sonic connector housing 63 such that O-rings 80, 82 are compressed thereby. In this regard, pressure is exerted by O-rings 80, 82 inwardly against the outer surface of plastic tube 74, thereby stabilizing and holding the plastic tube 74 in a centralized position. The outer diameter of the ultrasound transmission member 50 is only slightly smaller than the inner diameter of the plastic tube 74 such that the plastic tube 74 will limit possible side to side movement of the adjacent portion of the ultrasound transmission member 50, while allowing the ultrasound transmission member 50 to freely move longitudinally back and forth. Such limitation on side-to-side vibratory movement of the ultrasound transmission member 50, within the region of the plastic tube 74, serves to minimize the likelihood of fracture or breakage of the ultrasound transmission member 50, in the critical region closest to the point of connection to the ultrasound transducer or other ultrasound source.

Figure 4A:
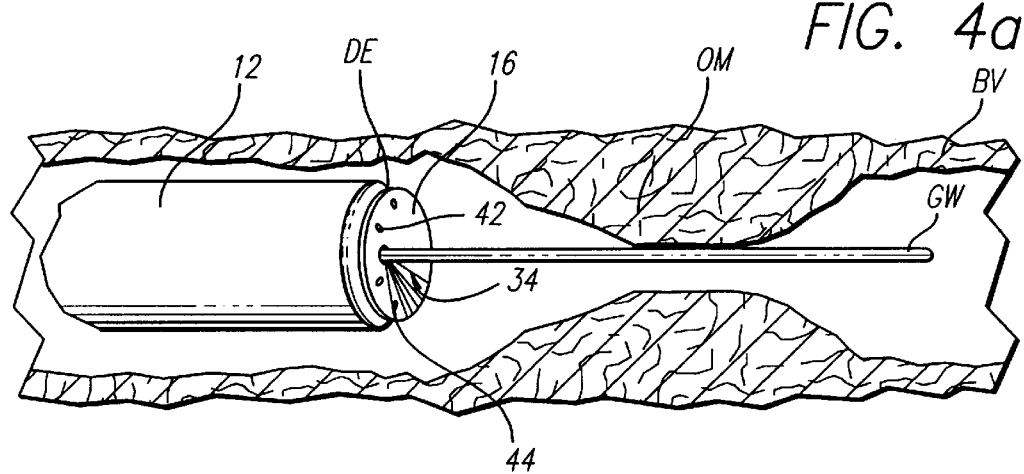
FIG. 4a–4c, is a step-by-step illustration of a presently preferred method for performing ultrasonic angioplasty-atherectomy using the catheter of the present invention.
Figure 4B:
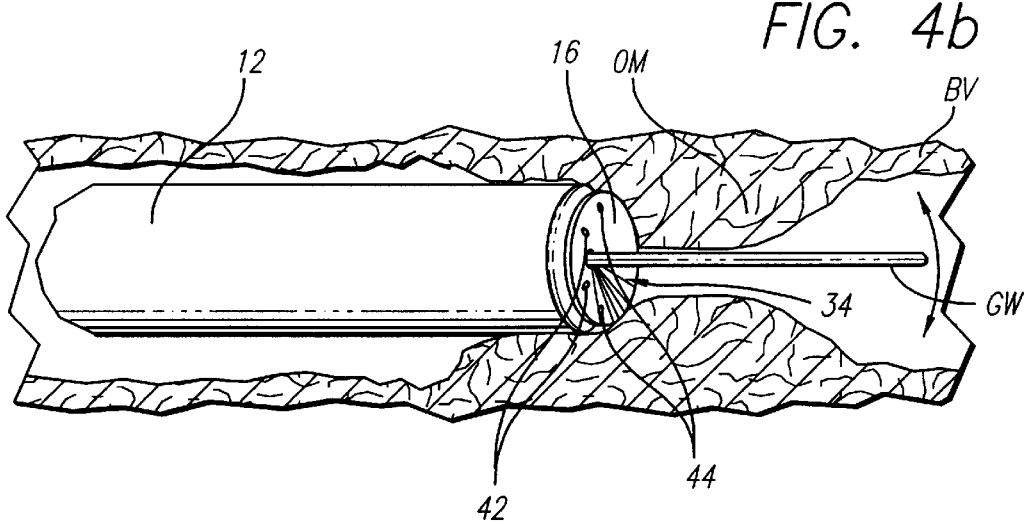
Figure 4C:
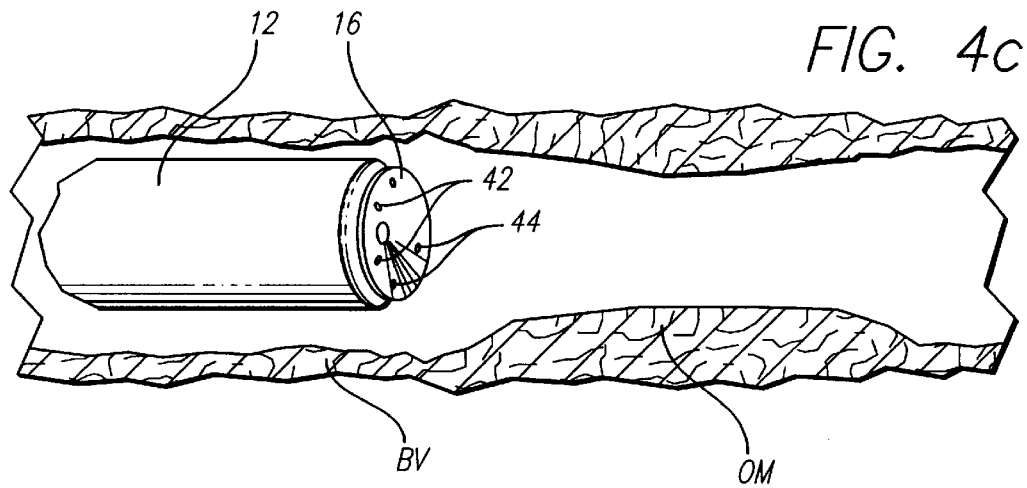

Thus, as shown in the step-wise illustration of FIGS. 4a–4c, the catheter shown in FIGS. 1–3 may be initially inserted, over a prepositioned guidewire GW having a preferred diameter of 0.008–0.025 inches, into an anatomical passageway such as a blood vessel BV wherein a quantity of atherosclerotic plaque or other obstructive matter OM is located. The guidewire GW is initially advanced through the obstructive matter OM, and the catheter device 10 is advanced to a point where the distal end DE of the catheter body 12 is immediately adjacent the obstructive matter OM (FIG. 4a).

Thereafter, an ultrasound transducer/generator or other source of ultrasonic energy attached to the sonic connector 52 is energized so as to pass ultrasonic energy through the ultrasound transmission member 50, to the distal tip member 16, thereby causing the distal tip member 16 to undergo ultrasonic vibratory movement. The catheter body 12 is subsequently advanced such that the vibrating peripheral edges of the concave indentation 34 of the vibrating tip member 16 cut into or separate the obstructive matter OM. As the vibrating peripheral edge of the concave distal tip member 16 severs or cuts away particles or quantities of the obstructive matter OM, the severed particles or quantities of obstructive matter may be aspirated through debris aspiration apertures 48, through debris/fluid aspiration pathways 46, through lumen 22, and out of the aspiration sidearm 62 located on proximal connector 18 (FIG. 4b). This will typically be accomplished by attaching a suction source to aspiration sidearm 62. A collection vessel may also be provided to collect the debris or other matter received through aspiration, to permit such matter to be subsequently analyzed for variation of the type and quantity of obstructive matter OM removed.

Also, apart from or during the procedure, quantities of irrigation fluid, medicaments, or other fluid may be infused through infusion sidearm 72, through lumen 26, through infusion outlet passageways 42, and out of infusion outlet apertures 44.

After the device 10 has been utilized to remove a sufficient amount of the obstructive matter OM to restore patency to the blood vessel BV or other anatomical passageway, the guidewire GW may be withdrawn and the catheter body 12 may be withdrawn from the body, thereby leaving the blood vessel BV in a restored state of improved patency.

It will be appreciated that the present invention has been described herein with reference to certain presently preferred embodiments of the invention, and no effort has been made to exhaustively describe all possible physical embodiments of the invention, or all possible components which may be utilized to practice the invention. In this regard, various modifications, additions, deletions and alterations may be made to the above-described embodiments without departing from the intended spirit and scope of the invention. Accordingly, it is intended that all such additions, deletions modifications and alterations be included within the scope of the following claims.

What is claimed is:

1. An ultrasonic device for removing obstructive matter from an anatomical passageway, said device comprising:

an elongate pliable catheter body having a proximal end, a distal end, and at least one lumen extending longitudinally therethrough;

a distal tip member fixedly attached to the distal end of said catheter body for engaging the obstructive matter, the distal tip member having a length selected so that the entire distal tip member is contained within the distal end of the catheter body, said distal tip member having a distal surface;

an ultrasound transmission member extending longitudinally through said catheter body to transmit ultrasound from an ultrasound source located adjacent the proximal end of said catheter body, through said catheter body, to said distal tip member; and at least one aspiration passageway extending longitudinally through said distal tip member from the proximal surface thereof to the distal surface thereof, said aspiration passageway being in communication with a lumen of said catheter such that matter located at the distal tip member may be aspirated, in the proximal direction, through said passageway and through said lumen of said catheter.

2. The ultrasonic device of claim 1 wherein said catheter body comprises a pliable plastic cardiovascular catheter sized to be inserted into a mammalian blood vessel.

3. The ultrasonic device of claim 1 wherein said catheter body comprises:

an outer tube having a proximal end, a distal end and a hollow lumen of a luminal diameter extending longitudinally therethrough; and an inner tube having an outer surface of an outer diameter, a proximal end, a distal end, and a hollow lumen extending longitudinally therethrough;

the outer diameter of said inner tube being smaller than the luminal diameter of said outer tube, and said inner tube being disposed within the lumen of said outer tube.

4. The ultrasonic device of claim 3 wherein said inner and outer tubes have central longitudinal axes, and said inner tube is positioned coaxially within the lumen of said outer tube.

5. The ultrasonic device of claim 4 wherein the lumenal diameter of the outer tube is at least 0.1 mm larger than the outer diameter of the inner tube, such that a luminal space of at least 0.1 mm exists between the lumenal surface of the outer tube and the outer surface of the inner tube.

6. The ultrasonic device of claim 3 wherein said distal tip member is in abutting contact with the distal ends of said inner and outer tubes; and wherein the lumen of said outer tube is in communication with said at least one aspiration passageway such that matter may be aspirated, in the proximal direction, through said aspiration passageway and through the lumen of said outer tube.

7. The ultrasonic device of claim 3 further comprising:

at least one outlet passageway extending longitudinally through said distal tip member from the proximal surface thereof to the distal surface thereof;

wherein the lumen of said outer tube is in connection with said at least one aspiration pathway such that matter may be aspirated in the proximal direction, through said aspiration pathway and through the lumen of said outer tube; and wherein the lumen of the inner tube is in communication with said at least one outlet passageway such that fluid may be infused through said lumen, through said outlet passageway, and out the distal end of said catheter device.

8. The device of claim 3 wherein the distal end of said inner tube terminates a spaced-distance short of the distal end of said outer tube, and wherein said distal tip member comprises:

a generally cylindrical member having a generally cylindrical outer surface of a diameter substantially the same as the lumenal diameter of said outer tube;

an annular depression formed about the periphery of the proximal surface of said tip member, said annular depression defining therewithin a central cylindrical proximal extension;

said distal tip member being inserted into the distal end of said catheter body such that outer cylindrical surface of said distal tip member is in abutment with the luminal surface of said outer tube, and such that the cylindrical proximal projection of said tip member is inserted into the distal end of the lumen of said inner tube.

9. The ultrasonic device of claim 8 wherein said at least one outlet passageway is formed longitudinally through said distal tip member, from the proximal surface of the central proximal projection thereof, to the distal surface thereof such that fluid may be infused from the lumen of the inner tube, through the outlet passageway, and out of the distal end of the device.

10. The ultrasonic device of claim 9 wherein the at least one aspiration passageway extends longitudinally through said distal tip member from the annular shoulder formed in the proximal surface thereof to the distal surface thereof and in communication with the lumenal space between the lumenal surface of the outer tube and the outer surface of the inner tube such that matter may be aspirated from the distal surface of the distal tip member, through the aspiration passageway and into the lumenal space.

11. The ultrasonic device of claim 10 further comprising:
a plurality of aspiration passageways, each of which is in communication with the lumenal space between the lumenal surface of the outer tube and the outer surface of the inner tube; and
a plurality of infusion passageways, each of which is in communication with the lumen of the inner tube;
whereby aspiration and infusion may occur simultaneously.

12. The ultrasonic device of claim 3 further comprising:
an infusion passageway formed through the distal tip member;
a plurality of lumina disposed in the catheter body such that separate lumina are in communication with the aspiration passageway and the infusion passageway;
whereby aspiration and infusion may be performed simultaneously.

13. The ultrasonic device of claim 12 further comprising:
a plurality of aspiration passageways each of which is in communication with a first lumen of the catheter body; and
a plurality of infusion passageways, each of which is in communication with a second lumen of the catheter body.

14. The ultrasonic device of claim 1 wherein said ultrasound transmission member is formed of material which exhibits super elastic properties in the range of temperatures encountered by said ultrasound transmission member during operation of said device.

15. The ultrasonic device of claim 14 wherein the material of which said ultrasound transmission member is formed comprises nickel-titanium alloy.

16. The device of claim 14 wherein said nickel titanium allow constitutes 50.8 anatomic percent nickel.

17. The ultrasonic device of claim 1 further comprising:
a guidewire passageway extending longitudinally through said distal tip member from the proximal end thereof to the distal end thereof, said guidewire passageway being in communication with a lumen of said catheter body such that a guidewire may be passed through the lumen of said catheter body and through said distal tip member.

18. The ultrasonic device of claim 17 further comprising:
a guidewire tube having a proximal end and a distal end, said guidewire tube being disposed in a lumen of said catheter body, the distal end of said guidewire tube being in communication with said guidewire passageway formed in said distal tip member, and the proximal end of said guidewire tube being in communication with a proximal guidewire outlet aperture formed in said device at a location proximal to the distal end of said catheter body.

19. The ultrasonic device of claim 18 wherein said proximal guidewire outlet aperture comprises an aperture formed in said pliable catheter body at a location 10–30 cm from the distal end of said catheter body.

20. The ultrasonic device of claim 18 wherein said proximal guidewire aperture is located adjacent the proximal end of said catheter body.

21. The ultrasonic device of claim 1 further comprising:
a proximal connector assembly mounted on the proximal end of said catheter body, said proximal connector assembly incorporating a sonic connector apparatus whereby an external ultrasound source may be connected to the proximal end of said ultrasound transmission member.

22. The ultrasonic device of claim 21 wherein said proximal connector assembly further comprises:
a suction outlet port located on said proximal connector assembly in communication with the lumen of said catheter body which is in communication with said aspiration passageway, to facilitate aspiration of matter in the proximal direction, through said aspiration passageway, through said lumen, and out of said suction port.

23. The ultrasonic device of claim 1 further comprising:
at least one outlet passageway separated from the aspiration passageway, the outlet passageway extending longitudinally through said distal tip member, from the proximal surface thereof to the distal surface thereof, said at least one outlet passageway being in communication with a lumen of said catheter body such that fluid may be infused through said lumen, through said outlet passageway, and out of the distal end of said catheter device.

24. The device of claim 23 further comprising:
a proximal connector assembly mounted on the proximal end of said catheter body, said proximal connector assembly incorporating a sonic connector apparatus whereby an external ultrasound source may be connected to the proximal end of said ultrasound transmission member and a fluid inlet port located on said proximal connector assembly in communication with the lumen of the catheter body which is in communication with said outlet passageway to facilitate infusion of fluid, in the distal direction, through said fluid inlet port, through said lumen, through said outlet passageway, and out of the distal end of said device.

25. The apparatus of claim 1 wherein said distal tip member is inserted into the distal end of a lumen of said catheter body, and secured to said catheter body by adhesive.

26. The apparatus of claim 1 wherein said distal tip member is inserted into the distal end of a lumen of said catheter body, and secured to said catheter body by heat fusing.

27. The ultrasonic device of claim 1 wherein the distal tip member comprises a concave indentation formed in the distal surface.

28. The ultrasonic device of claim 1 further comprising:
an infusion passageway formed through the distal tip member;
a plurality of lumina disposed in the catheter body such that separate lumina are in communication with the aspiration passageway and the infusion passageway;
whereby aspiration and infusion may be performed simultaneously.

29. The ultrasonic device of claim 28 further comprising:
a plurality of aspiration passageways each of which is in communication with a first lumen of the catheter body; and a plurality of infusion passageways, each of which is in communication with a second lumen of the catheter body.

30. A method for removing obstructive matter from an anatomical passageway, said method comprising the steps of:

a) providing an ultrasonic catheter device which comprises:

an elongate pliable catheter body having a proximal end, a distal end, and at least one lumen extending longitudinally therethrough;

a distal tip member fixedly attached to the distal end of said catheter body for engaging the obstructive matter, the distal tip member having a length selected so that the entire distal tip member is contained within the distal end of the catheter body, said distal tip member having a distal surface;

an ultrasound transmission member extending longitudinally through said catheter body to transmit ultrasound from an ultrasound source located adjacent the proximal end of said catheter body, through said catheter body, to said distal tip member;

at least one aspiration passageway extending longitudinally through said distal tip member from the proximal surface thereof to the distal surface thereof, said aspiration passageway being in communication with a lumen of said catheter such that matter located at the distal tip member may be aspirated, in the proximal direction, through said passageway and through said lumen of said catheter;

b) inserting said catheter body into said anatomical passageway wherein the obstructive material is located;

c) advancing said catheter body to a point where said distal tip member is located adjacent the obstructive matter to be removed;

d) passing ultrasound through said ultrasound transmission member through said distal tip member, thereby causing said distal tip member to undergo ultrasonic vibratory movement;

e) advancing said catheter body such that the distal surface of said distal tip member comes into contact with said obstructive matter, and such that the ultrasonic vibratory movement of said distal tip member facilitates severance of a portion of said obstructive matter; and f) causing a severed portion of said obstructive matter to be aspirated in the proximal direction, through said aspiration passageway, and through a lumen of said catheter body.

31. The method of claim 30 wherein the catheter provided in step a) further comprises at least one outlet passageway which extends longitudinally through said distal tip member, in communication with a lumen of said catheter body, and wherein said method further comprises:

g) infusing fluid through said lumen of said catheter body and out of said outlet passageways, in the area of said obstructive matter.

32. The method of claim 31 wherein steps f and g are conducted separately.

33. The method of claim 31 wherein steps f and g are conducted concurrently.

* * * * *